United States Patent [19]

Koch

[11] Patent Number: 4,820,637

[45] Date of Patent: Apr. 11, 1989

[54] DETECTION OF FUNGI AND/OR ALGAE WITH STILBENE HAVING AT LEAST 4 SULPHO GROUPS

[75] Inventor: Herbert A. Koch, Düsseldorf, Fed. Rep. of Germany

[73] Assignee: Ciba-Geigy Corporation, Ardsley, N.Y.

[21] Appl. No.: 25,133

[22] Filed: Mar. 12, 1987

[30] Foreign Application Priority Data

Mar. 21, 1986 [CH] Switzerland ................. 1141/86

[51] Int. Cl.[4] .............................. C12Q 1/02
[52] U.S. Cl. ........................... 435/29; 435/4; 435/810
[58] Field of Search ................ 435/4, 29, 810

[56] References Cited

U.S. PATENT DOCUMENTS 3,406,118 10/1968 Tscharner et al. .......... 252/301.2

OTHER PUBLICATIONS

Chemical Abstracts, 100:82253e (1984).
U. Gisi, Pflkrankh 1/75, pp. 30–47.
U. Gisi, Pflkrankh 6/7/75, pp. 355–377.
U. Gisi, Pflkrankh, et al., Microscopica 77:402–419 (1976).
H. Holländer, et al., Mycopathologia 88:134–134 (1984).
J. E. Monheit, et al., Arch. Pathol. Lab. Med. 108:616–618 (1984).
H. Schlegel, et al., Zbl. Mikrobiol. 137:36–41 (1982).
H. Maeda, et al., J. of Biochem 62: (2)276–278 (1967).
H. M. Wilson, Science, vol. 151, p. 212 (1965).
A. M. Paton, et al., Nature 204:803–804 (1964).
M. A. Darken, Science 133:1704–1705 (1961).
P. G. Jones, et al., Clin. Microbiol. Newsletter, vol. 9, p. 6 (1987).
H. A. Koch, et al., Abstract 1986 ASM Annual Meeting (3/1986).

Primary Examiner—Sidney Marantz
Attorney, Agent, or Firm—Irving M. Fishman; JoAnn Villamizar

[57] ABSTRACT

The invention relates to a method for the detection of fungi and algae in animal or human tissues and body fluids, to preparations containing an optical whitening agent suitable for the method, and to a test pack for performing the method. The tissue sections or body fluid samples to be examined are treated with an optical whitening agent and observed using a fluorescence microscope. The invention permits a rapid and reliable diagnosis of fungal infections.

11 Claims, No Drawings

DETECTION OF FUNGI AND/OR ALGAE WITH STILBENE HAVING AT LEAST 4 SULPHO GROUPS

The invention relates to a method for the detection of fungi and algae in animal and human tissues and body fluids, to preparations containing an optical whitening agent suitable for the method, and to a test pack for performing the method.

An accurate diagnosis of the cause of an infection in animals and humans is of crucial importance when choosing the treatment to be adopted. The best method for a reliable diagnosis consists in isolating the causative organism of the infection from clinical preparations and identifying it morphologically. Such an ideal situation is, however, seldom achieved because the isolation is complicated and the identification often uncertain. Even a tentative diagnosis of fungal infections requires comprehensive examination of tissue specimens or body fluids, for example serological tests using a series of different antibodies that recognize certain antigens of fungi selectively.

There is a widespread need for a rapid and reliable diagnosis that could replace the complicated and time-consuming serological tests or at least limit them to those cases in which accurate information on the genus of the fungal organism causing the infection is necessary. Such a rapid diagnosis is important, for example, in the examination of material arising during operations, gynaecological swabs for analysing a discharge caused by fungi, dermatological swabs in the case of suspected dermatomycoses, paediatric swab material and other examination material from newborn babies and debilitated children with general infections and suspected mycoses on the mucous membranes, for example Candida-induced thrush on oral and pharyngeal mucous membranes and the oesophagus and trachea in the case of leukaemias and other tumour diseases in chidren. a rapid diagnosis is also important in internal, oncological and surgical practice in the examination of tissue material taken from patients with suspected opportunistic fungal infections, for example in the case of AIDS patients for recognizing, especially, candidiasis in the form of an oesophagitis and bronchitis, in the case of patients undergoing cytostatic treatment of tumour diseases and in the case of patients undergoing treatment with antibiotics and/or immunosuppressants, also in the case of suspected mycoses, especially candidiasis, in the form of thrush on mucous membranes, in geriatrics when examining patients with lowered resistance who have generalised mycoses on the skin and/or mucous membranes, and in the case of suspected skin and organ infections caused by algae, for example protothecosis.

A diagnosis of fungal diseases is also important in the case of livestock and pets, for example when investigating mastitis in cattle and in the case of fungal diseases, for example, in dogs, ornamental birds and rare and valuable zoo animals. A simple and reliable method of identifying fungi is also important when testing potentially antifungal therapeutic agents on laboratory animals, for example mice and rats, having artificially produced fungal infections.

The present invention now permits such a rapid and reliable diagnosis of fungal infections. The invention relates to a method for the detection of fungi and algae, characterised in that animal or human tissue or body fluid is treated with an optical stilbene whitening agent having at least 4 sulpho groups or with a salt thereof and is examined using a fluorescence microscope.

Optical whitening agents are organic compounds that are colourless or have only a slightly visible colouring and that absorb ultraviolet light, for example of a wavelength of from 340 to 400 nm, and give off this absorbed energy again in the form of visible light, for example of a wavelength of from 400 to 440 nm. Good optical whitening agents are distinguished by a high quantum yield. Optical whitening agents belong, for example, to the class of stilbenes, coumarins and carbostyril compounds, 1,3-diphenyl-2-pyrazolines, naphthalimides, or benzoxazolyl compounds or other heteroaromatically substituted aromatic compounds or ethylene compounds, and always have a conjugated $\pi$-electron system.

The optical whitening agents of the present invention belong to the class of substituted stilbenes and carry at least 4, for example from 4 to 6, sulpho groups. These sulpho groups impart good water-solubility to the optical whitening agents. The manufacture of optical stilbene whitening agents having at least 4 sulpho groups and their salts is known and is described, for example, in review articles and specialist books, for example in "Fluorescent Whitening Agents" (editors R. Anliker and G. Müller, Georg Thieme Verlag, Stuttgart 1975).

Examples of optical stilbene whitening agents having at least 4 sulpho groups are compounds of the formula

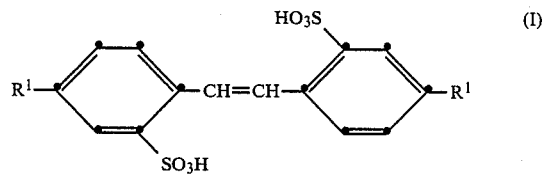

in which $R^1$ represents an aromatic or heteroaromatic substituent carrying at least one sulpho group, for example a substituted phenyl radical, pyridyl radical or triazolyl radical, for example a sulpho-substituted 4-phenyl-1,2,3-triazol-2-yl radical, or represents an amino group substituted by an aromatic or heteroaromatic radical having at least one sulpho group, for example substituted triazinylamino, for example 2,4-disubstituted 1,3,5-triazin-6-ylamino having at least one sulpho group, and the two radicals $R^1$ may be the same or different, and also compounds of the formula

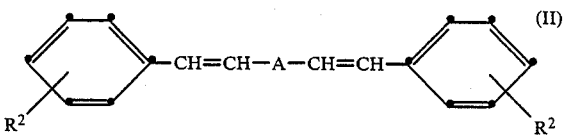

in which A represents a 1,4-phenylene or 4,4'-biphenylylene radical substituted by sulpho groups and $R^2$ represents sulpho, hydroxy, lower alkoxy, for example methoxy, hydroxy-lower alkoxy, for example 2-hydroxyethoxy, halogen, for example chlorine, cyano, carboxy, lower alkoxycarbonyl, for example methoxycarbonyl or ethoxycarbonyl, or carbamoyl, or has the meanings of $R^1$, and the radicals $R^2$ may be the same or different and, in addition, may occur several times.

Lower alkyl and the lower alkyl radical in a lower alkoxy group has from 1 to 7, preferably from 1 to 4, carbon atoms and is, for example, methyl, ethyl, propyl, isopropyl or butyl. Preferred substituents of phenyl, pyridyl, triazolyl or triazinyl groups are, for example, the radicals mentioned hereinafter under $R^3$.

Salts are especially water-soluble salts, for example alkali metal salts, such as sodium or potassium salts, but also ammonium salts.

Preferred in the method of the present invention are optical stilbene whitening agents of the formula

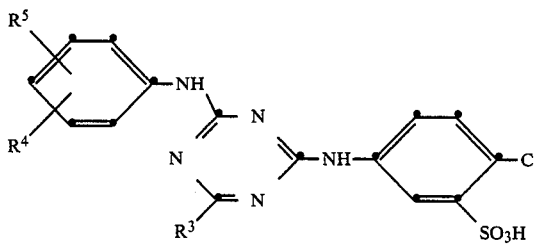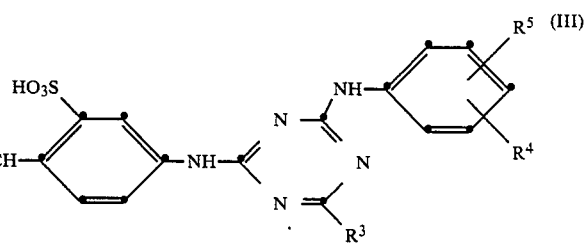

in which $R^3$ represents hydroxy, lower alkoxy, for example methoxy, hydroxy-lower alkoxy, for example 2-hydroxyethoxy, lower alkoxy-lower alkoxy, for example 2-methoxyethoxy, lower alkylamino, for example methylamino, di-lower alkylamino, for example dimethylamino, hydroxy-lower alkylamino, for example 2-hydroxyethylamino or 2-hydroxypropylamino, lower alkyl-hydroxy-lower alkyl-amino, for example methyl-2-hydroxyethyl-amino, di(hydroxy-lower alkyl)amino, for example di(2-hydroxyethyl)amino or di(2-hydroxypropyl)amino, lower alkoxy-lower alkylamino, for example 2-methoxyethylamino, lower alkyl-lower alkoxy-lower alkyl-amino, for example methyl-2-methoxyethyl-amino, di(lower alkoxy-lower alkyl)amino, for example di(2-methoxyethyl)amino, morpholino or phenylamino which is optionally substituted in the phenyl ring by sulpho groups, for example anilino, 2-, 3- or 4-sulphophenylamino or 2,5-disulphophenylamino, $R^4$ represents sulpho, for example 2-, 3- or 4-sulpho, and $R^5$ represents hydrogen, sulpho, for example 4- or 5-sulpho, or an annulated phenyl ring, for example 2,3- 3,4- or 5,6-benzo, and the two radicals $R^3$, the two radicals $R^4$ and the two radicals $R^5$ each may be the same or different, and also the water-soluble salts, for example alkali salts, such as sodium and potassium salts, derived therefrom.

Particularly preferred in the method of the present invention are optical stilbene whitening agents of the formula III in which $R^3$ represents hydroxy-lower alkylamino, for example 2-hydroxyethylamino, di(hydroxy-lower alkyl)amino, for example di(2-hydroxyethyl)amino, or phenylamino substituted by sulpho, for example 3-sulphophenylamino, $R^4$ represents sulpho, for example 2-, 3- or 4-sulpho, and $R^5$ represents hydrogen, sulpho, for example 5-sulpho, or an annulated phenyl ring, for example 2,3-benzo, and its readily water-soluble salts, for example sodium salts.

The present invention relates especially to a method using the compound of the formula III in which $R^3$ represents di(2-hydroxyethyl)amino or 3-sulphophenylamino, $R^4$ represents 3-sulpho and $R^5$ represents hydrogen, and its water-soluble salts, preferably the sodium salt.

The very especially preferred optical stilbene whitening agent is known under the name diaethanol and is named systematically as the sodium salt of 4,4'-bis[2-di(2-hydroxyethyl)amino-4-(3-sulphophenylamino)-1,3,5-triazin-6-ylamino]-stilbene-2,2'-disulphonic acid.

The compound can be manufactured, for example, in the manner described in U.S. Pat. No. 3,406,118.

Animal or human tissue that can be stained by the present method for the detection of fungi and algae may originate from any organs or parts of the body and is examined, for example, in the form of microtome tissue sections of freeze-dried tissue material or dehydrated tissue embedded in paraffin or in the form of klatsch or swab preparations. Body fluids in which fungi and algae can be detected by the present method are, for example, blood, sputum, bronchial secretions, lymph fluid, cerebrospinal fluid and other punctates, sweat, lacrimal fluid, intra-ocular fluid, urine or faeces.

Especially preferred is a method for detecting fungi and algae in human tissue or body fluids.

The tissue sections, or preparations made by some other method, for example swabs, klatsch preparations or solid constituents isolated from body fluids, are treated preferably with an aqueous solution containing from 0.05 to 5%, preferably from 0.1 to 2%, of the optical whitening agent, for example in water, in a salt solution, for example in buffered physiological saline, or in a histological fixing solution, for example in 10% aqueous formaldehyde solution or an aqueous-alcoholic solution, for a few minutes, for example from 2 to 30 minutes, at room temperature or slightly elevated temperature, for example up to 50° C. Excess optical whitening agent is, if appropriate, washed away, for example with water or a salt solution, for example buffered physiological saline. If desired, the preparations to be examined are then counterstained with one of the customary dyestuffs suitable for staining tissue sections or cell constituents, for example with methylene blue, toluidine blue, fuchsin, methyl violet or the like, but preferably with Evans blue, in order to enhance the contrast.

The preparations so treated are observed under a microscope in reflected visible blue light or UV light (epiillumination), preferably in the range of from 340 to 450 nm. The greenish fluorescent colour of characteristic structures of fungi or algae that can be observed indicates immediately the presence of such causative organisms. In most cases it is possible to infer the genus and species of the fungus from the morphology of the stained fungal constituents. If desired, the images visible under the microscope can be recorded photographically with customary commercially available colour-sensitive films.

The described method according to the invention is distinguished by a simple, time-saving procedure and a high degree of reliability and is thus clearly superior to other methods of diagnosing fungal infections. Compared with conventional staining methods, for example the customarily used Gomori methenamine-silver staining method or periodic acid-Schiff staining method, the method according to the invention has the advantage that fungi are stained selectively, the fluorescent staining stands out better against the unstained background and the method gives reliable results in less than 2 hours whereas conventional staining methods require 24 hours or more. The method according to the invention is clearly superior to staining with Blankophor ® BA or Calcofluor ® white M2R new, which are both triazinylaminostilbene whitening agents having only 2 sulpho groups and have been recommended for staining animal and human tissue, because according to the invention all fungi and algae are stained selectively, whereas the mentioned whitening agents do not stain some fungi, or stain them only poorly, and stained fungi are not readily recognisable in the tissue.

In other to perform the method, all that is required are readily available reagents and a simple fluorescence microscope, as is usually available in a microbiological or medical laboratory.

Positive fluorescence with the preferred water-soluble optical whitening agent, diaethanol, is observed in the case of all mycoses, for example Lobo's mycosis of the skin, blastomycosis of the lung, trichosporosis of the spleen, candidiasis of the kidney, histoplasmosis of the lung, actinomycosis of the liver, aspergillosis of the kidney, and also adiaspiromycosis, coccidioidomycosis, cryptococcosis, rhinosporidiosis, madura foot, and many others. It is likewise possible tto stain isolated and cultured fungi, for example the representatives belonging to the genus Eumycota, for example Zygomycetes, Endomycetes, Ascomycetes or Deuteromycetes (Fungi imperfecti), in particular *Blastomyces dermatidis, Candida albicans, Aspergillus fumigatus, Sporotrichum schenkii, Trichophyton mentagrophytes, Trichophyton quinckeanum, Microsporum canis, Torulopsis glabrata*, and others, and also algae, for example *Prototheca*. In contrast, and surprisingly, no staining is observed in the case of bacteria and parasites; the following, especially, are not stainable: Staphylococci, for example *Staph. aureus* K 1326, Streptococci, for example *Strept. faecalis*, Salmonellae, for example Salmonella K 1385, Coli bacteria, for example *Escherichia coli* K 1322, Pseudomonadeae, for example Pseudomonas K 1407, and Mycobacteria, for example *Mycobact. smegmatis*. It is also noteworthy that important pathogenic causative organisms that do not belong to the fungi, for example *Pneumocystis carinii, Giardia lamblia, Leishmania donovani, Leish. chagasi* and *Leish. infantum*, are not stained.

The invention also relates to preparations containing an optical whitening agent suitable for carrying out the method. Such preparations are, for example, aqueous solutions of optical stilbene whitening agents having at least 4 sulpho groups as described hereinbefore, and also solid mixtures, for example powdery or granular mixtures.

Aqueous solutions according to the invention contain, for example, 0.05% to 5%, preferably 0.1–2%, for example 1%, of the optical stilbene whitening agent and, if desired, further compounds, for example salts, for example sodium chloride, potassium chloride, sodium sulfate, sodium or potassium dihydrogen phosphate, disodium or dipotassium hydrogen phosphate, or other buffer compounds, for example N-2-hydroxyethylpiperazine-N'-2-ethanesulphonic acid, 3-morpholinopropanesulphonic acid, N-tris(hydroxymethyl)-methyl-glycine or tris(hydroxymethyl)aminomethane, and their alkali metal salts, for example sodium salts, and/or acid addition salts, for example hydrochlorides, respectively, denaturing and/or solubilising organic solvents, for example methanol or ethanol, and fixing compounds, for example formaldehyde, and also, if desired, diluting agents, for example urea, wetting agents, for example aliphatic or aromatic sulfonates, or complexing agents for calcium ions, for example sodium ethylenediamine-tetraacetate. The concentration of the optical stilbene whitening agent in the aqueous solution may also be more than 5%, for example up to 20%. Such solutions have to be diluted before they can be applied to the method of the invention.

Solid mixtures according to the invention are mixtures of optical stilbene whitening agents with the salts mentioned hereinbefore, for example with sodium chloride, potassium chloride and/or buffer salts, such as sodium dihydrogen phosphate and disodium hydrogen phosphate, or with organic, solid buffer compounds, for example with tris(hydroxymethyl)aminomethane and the corresponding hydrochloride. These mixtures have to be dissolved in water before they can be applied to the method of the invention.

Preferred preparations are aqueous solutions of the optical stilbene whitening agents described as preferred hereinbefore, for example of 4,4'-bis[2-di(2-hydroxyethyl)amino-4-(3-sulphophenylamino)-1,3,5-triazin-6-ylamino]-stilbene-2,2'-disulphonic acid, known as diaethanol. Especially preferred are such solutions containing 0.1–2%, for example 1%, of the preferred whitening agent in distilled water or in phosphate-buffered physiological saline.

The preparations according to the invention are obtained according to methods of dissolving, mixing, grinding, granulating and/or lyophilising known per se.

The invention also relates to test kits for carrying out the method according to the invention. Such test kits contain, for example, an optical stilbene whitening agent having at least 4 sulpho groups as such or in form of a preparation according to the invention as described hereinbefore, dyestuffs or staining solutions for counter-staining, buffer substances or buffer solutions, and also auxiliary devices, such as pipettes, slides and cover glasses for microscopes, instructions for carrying out the method according to the invention, comparison specimens and the like.

Test kits according to the invention may also contain serological test solutions, for example polyclonal or monoclonal antibody solutions, with which a first, tentative identification of a fungal genus derived from staining with the optical stilbene whitening agent can be additionally confirmed. Such polyclonal and monoclonal antibodies, which are directed against marker antigens of the various fungal genera and bind specifically to the corresponding fungi, are known or can be manufactured according to known processes. It is preferable to use fluorescence-marked antibodies, for example antibodies marked with rhodamine- or fluorescein-isothiocyanate, in order to be able to render antigen/antibody reactions readily visible under the fluorescence microscope. The test kits may contain also solutions of antibodies which react specifically with certain bacteria or certain protozoa. Preferably are used those fluorescence-labelled antibodies, the fluorescence colour of which can be distinguished from the fluorescence colour of the optical stilbene whitening agent of the invention, for example antibodies labelled with rhodamine-isothiocyanate, in order to be able to screen for fungi and bacteria or protozoa, respectively, side by side in one operation.

The following Examples illustrate the invention but do not limit its scope in any way.

EXAMPLE 1

Staining of fungi in tissue sections

Pieces of tissue, for example biopsy material, are embedded in paraffin in capsules in the usual manner, the paraffin is hardened and the blocks are cut in a microtome to a layer thickness of from 3 to 4 μm. The paraffin sections are applied to slides, stretched in a water bath and dried, and the paraffin is washed out with xylene three times, then with alcohol, alcohol/water mixtures, water and finally with phosphate-buffered physiological saline (PBS). Instead of paraffin sections it is also possible to apply approximately 10 μm thick microtome sections of deep-frozen tissue material and to condition them with PBS.

The tissue sections are saturated with a solution of 1% diaethanol in PBS, pH 7. After from 10 to 30 minutes the sections are rinsed with PBS, then treated with a 0.2% solution of Evans blue in PBS and, after half a minute, washed with PBS again. The sections in water are placed on slides and covered and then sealed with nail varnish. The tissue sections are observed under an Olympus ® BHTU microscope in epifluorescent light. The cell walls and cell plasma of fungi are stained with a fluorescent greenish or greenish or greenish-yellowish colour while the background assumes a light brownish colour, so producing a good contrast. The photomicrographs are taken with a Leica small-format camera using Kodak colour film ASA 400.

EXAMPLE 2

Staining of material from culture broths or body fluids

Material to be examined is spread onto a slide, air-dried, heat-fixed with a flame and covered for 1 minute with methanol. The slide is covered with a layer of an aqueous solution of 0.1% diaethanol. After 5 minutes, the staining solution is poured off and the slide is rinsed with water and air-dried. The specimen is covered with a cover glass and observed under a Dialux-20 ® microscope of 40 times magnification with reflected UV light (epiillumination) that has passed through a filter H2 (wavelength 390–490 nm). The contrast is advantageously improved when the sample stained with the whitening agent is treated for half a minute with a 0.2% aqueous solution of Evans blue and washed with water before drying.

EXAMPLE 3

Examination of optical whitening agents as stains for fungi

*Candida albicans* K 1133, *Aspergillus fumigatus* K 76 and *Microsporum canis* K 240 are cultivated on Mycophil agar, suspended in physiological saline for the series of tests, and mixed in equal parts with a suspension of potted mouse kidneys. Each time 1 drop of this mixture is put on a slide, dried in the air, drawn three times through a flame for fixing, covered for 1 minute with methanol, and washed with distilled water. The fixed fungal sample is covered for 5 minutes with a 1% aqueous solution of the optical whitening agent to be examined, washed with phosphate-buffered physiological saline (PBS), covered for half a minute with a 0.2% solution of Evans blue in PBS, washed with PBS, and covered with a cover glass. The sample is observed under a Dialux-20 ® microscope of 40 times magnification with reflected UV light (epiillumination, 390–490 nm).

The intensity of the fluorescence of the fungi in relation to the staining of the background organ cells is rated on an arbitrary scale. 2–3 experiments are performed per fungus, and a mean value is calculated. The following results are obtained:

Very good staining with
4,4'-bis-[2-di(2-hydroxyethyl)amino-4-(3-sulphophenylamino)-1,3,5-triazin-6-ylamino]-stilbene-2,2'-disulfonic acid sodium salt (diaethanol), and
4,4'-bis-[2,4-di(3-sulphophenylamino)-1,3,5-triazin-6-ylamino]-stilbene-2,2'-disulfonic acid sodium salt.

Good staining with
4,4'-bis-[2-di(2-hydroxyethyl)amino-4-(4-sulfo-1-naphthylamino)-1,3,5-triazin-6-ylamino]-stilbene-2,2'-disulfonic acid sodium salt,
4,4'-bis-[2-di(2-hydroxyethyl)amino-4-(2,5-disulphophenylamino)-1,3,5-triazin-6-ylamino]-stilbene-2,2'-disulfonic acid sodium salt,
4,4'-bis-[2-(2-hydroxyethyl)amino-4-(3-sulphophenylamino)-1,3,5-triazin-6-ylamino]-stilbene-2,2'-disulfonic acid sodium salt, and
4,4'-bis-[2-di(2-hydroxyethyl)amino-4-(4-sulphophenylamino)-1,3,5-triazin-6-ylamino]-stilbene-2,2'-disulfonic acid sodium salt.

Medium staining with
4-[2-di(2-hydroxyethyl)amino-4-methoxy-1,3,5-triazin-6-ylamino]-4'-[2-di(2-hydroxyethyl)amino-4-(2-sulphoethylamino)-1,3,5-triazin-6-ylamino]-stilbene-2,2'-disulfonic acid sodium salt,
4,4'-bis-[2-morpholino-4-(2,5-disulphophenylamino)-1,3,5-triazin-6-ylamino]-stilbene-2,2'-disulfonic acid sodium salt,
4,4'-bis-[2-di(2-hydroxypropyl)amino-4-(3-sulphophenylamino)-1,3,5-triazin-6-ylamino]-stilbene-2,2'-disulfonic acid sodium salt, and
4,4'-bis-[2-di(2-hydroxypropyl)amino-4-(4-sulphophenylamino)-1,3,5-triazin-6-ylamino]-stilbene-2,2'-disulfonic acid sodium salt.

Stilbene whitening agents with one 2 sulphonic acid functions or with carboxy or ammonium groups in place of sulpho groups and stilbene whitening agents without the 2,4-disubstituted 1,3,5-triazin-6-ylamino radical give less staining or no staining at all.

EXAMPLE 4

Solution of diaethanol in phosphate-buffered physiological saline 10.0 g 4,4'-bis-[2-di(2-hydroxyethyl)amino-4-(3-sulphophenylamino)-1,3,5-triazin-6-ylamino]-stilbene-2,2'-disulfonic acid sodium salt (diaethanol, free of sodium chloride), 0.2 g potassium chloride, 8.0 g sodium chloride, 1.44 g disodium hydrogen phosphate dihydrate and 0.2 g potassium dihydrogen phosphate are dissolved in 1 l distilled water.

The same solution may also be prepared with crude diaethanol containing sodium chloride (13%) and water (5–10%). The amount of diaethanol and salt is adjusted accordingly.

EXAMPLE 5

Test Kit

A test kit for staining fungi in bulk contains:
Screw cap flask containing 250 ml of a 1% solution of diaethanol in phosphate-buffered saline.

Screw cap flask containing 250 ml of a 0.2% solution of Evans blue in phosphate-buffered saline.
Instructions for carrying out the staining method.

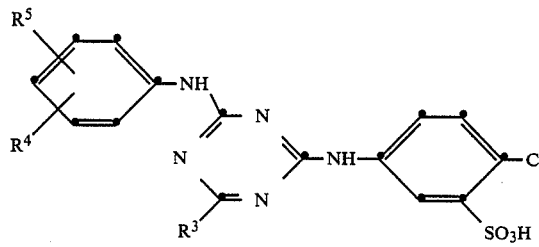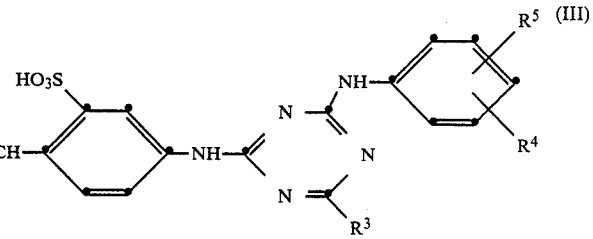

EXAMPLE 6

Test kit

A test kit for staining fungi in small portions contains:

20 tear wrapper packages of polyethylene coated aluminium foil, each containing 1 ml of a 1% solution of diaethanol in phosphate-buffered saline.

20 tear wrapper packages of polyethylene coated aluminium foil, each containing 1 ml of a 0.2% solution of Evans blue in phosphate-buffered saline.

Instructions for carrying out the staining method.

I claim:

1. A method for the detection of fungi or algae or both, comprising treating an animal or human tissue or body fluid with an optical stilbene whitening agent having at least 4 sulpho groups or a salt thereof and examining the animal or human tissue or body fluid using a fluorescence microscope.

2. The method according to claim 1, wherein said optical stilbene whitening agent has from 4 to 6 sulpho groups or a salt thereof.

3. The method according to claim 1, wherein said optical stilbene whitening agent is of the formula

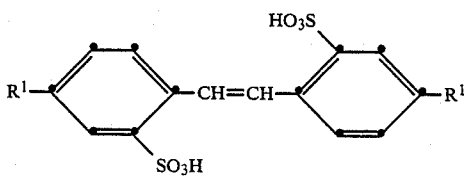

in which $R^1$ represents an aromatic or heteroaromatic substituent carrying at least one sulpho group or represents an amino group substituted by an aromatic or heteroaromatic radical having at least one sulpho group, and the two radicals $R^1$ may be the same or different, or of the formula

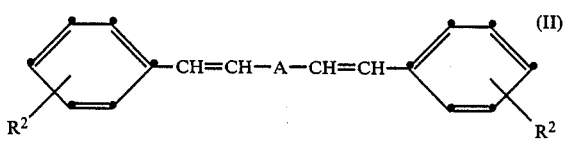

in which A represents a 1,4-phenylene or 4,4'-biphenylylene radical substituted by sulpho groups and $R^2$ represents sulpho, hydroxy, lower alkoxy, hydroxy-lower alkoxy, halogen, cyano, carboxyl, lower alkoxy-carbonyl or carbamoyl or has the meanings of $R^1$, and the radicals $R^2$ may be the same or different and, in addition, may occur several times, or a salt thereof.

4. The method according to claim 1, wherein said optical stilbene whitening agent is of the formula in which $R^3$ represents hydroxy, lower alkoxy, hydroxy-lower alkoxy, lower alkoxy-lower alkoxy, lower alkylamino, di-lower alkylamino-, hydroxy-lower alkylamino, lower alkyl-hydroxy-lower alkyl-amino, di(hydroxy-lower alkyl)amino, lower alkoxy-lower alkylamino, lower alkyl-lower alkoxy-lower alkylamino, di(lower alkoxy-lower alkyl)amino, morpholino or phenylamino which is optionally substituted in the phenyl ring by sulpho groups, $R^4$ represents sulpho, and $R^5$ represents hydrogen, sulpho or an annulated phenyl ring, and the two radicals $R^3$, the two radicals $R^4$ and the two radicals $R^5$ each may be the same or different, or a water-soluble salt thereof.

5. The method according to claim 4, wherein $R^3$ represents hydroxy-lower alkylamino, di(hydroxy-lower alkyl)amino or sulphophenylaino, $R^4$ represents sulpho and $R^5$ represents hydrogen, sulpho or an annulated phenyl ring, or a water-soluble salt thereof.

6. The method according to claim 4, wherein $R^3$ represents di(2-hydroxy-ethyl)amino or 3-sulpho-phenylamino, $R^4$ represents 3-sulpho and $R^5$ represents hydrogen, or a water-soluble salt thereof.

7. The method according to claim 1, wherein said optical stilbene whitening agent is the sodium salt of 4,4'-bis[2-di(2-hydroxyethyl)amino-4-(3-sulpho-phenylamino)-1,3,5-triazin-6-ylamino]-stilbene-2,2'-disulphonic acid.

8. A method of staining fungi or algae or both in a human tissue or body fluid comprising treating said tissue or body fluid with an optical stilbene whitening agent having at least four sulfo groups or a salt thereof.

9. A test kit for use in the detection of fungi or algae or both in an animal or human tissue or body fluids comprising an optical stilbene whitening agent having at least 4 sulpho groups, or a salt thereof, a dyestuff and at least one of a serological test solution and instructions for carrying out said detection of fungi and algae.

10. The test kit according to claim 9 wherein said optical stilbene whitening agent is in the form of an aqueous solution containing between 0.05% and 5% of the optical stilbene whitening agent and further comprising at least one of a salt, an organic buffer, an organic solvent and a fixing agent.

11. The test kit according to claim 9 wherein said optical stilbene whitening agent is the sodium salt of 4,4'-bis[2-di(2-hydroxyethyl)amino-4-(3-sulpho-phenylamino)-1,3,5-triazin-6-ylamino]-stilbene-2,2'-disulphonic acid.

* * * * *